United States Patent [19]

Saito

[11] Patent Number: 5,031,448
[45] Date of Patent: Jul. 16, 1991

[54] EXHAUST VALVE FOR SUPERCRITICAL FLUID CHROMATOGRAPH

[75] Inventor: Toshinori Saito, Tokyo, Japan

[73] Assignee: JEOL Ltd., Tokyo, Japan

[21] Appl. No.: 465,949

[22] Filed: Jan. 16, 1990

[30] Foreign Application Priority Data

Jan. 20, 1989 [JP] Japan ..................................... 1-11558

[51] Int. Cl.$^5$ .............................................. G01N 15/00
[52] U.S. Cl. .................. 73/61.1 C; 73/23.35; 73/23.42
[58] Field of Search ............. 73/23.35, 23.42, 61.1 C, 73/; 422/89; 436/161; 137/240; 55/386, 67; 210/198.2, 656

[56] References Cited

U.S. PATENT DOCUMENTS

| | | | |
|---|---|---|---|
| 4,454,749 | 6/1984 | Guillemin et al. | 73/61.1 C |
| 4,597,943 | 7/1986 | Sugiyama et al. | 73/61.1 C |
| 4,835,109 | 5/1989 | Trisciani et al. | 73/61.1 C |

FOREIGN PATENT DOCUMENTS 0130466  5/1990  Japan ............................... 73/61.1 C

OTHER PUBLICATIONS

"Supercritical Fluid Chromatography with Small Particle Diameter Packed Columns", Dennis R. Gere, Analytical Chemistry, vol. 54, No. 4, Apr. 1982, pp. 736-740.

Primary Examiner—Hezron E. Williams
Attorney, Agent, or Firm—Webb, Burden, Ziesenheim & Webb

[57] ABSTRACT

An exhaust valve for a supercritical fluid chromatography apparatus. The exhaust valve is a constant-pressure release valve which maintains the pressure inside the flow passage system of the apparatus constant. Eluates are discharged via the valve. An organic solvent effective at atmospheric pressures, such as toluene, dichloromethane, or benzene, which readily dissolves the analyzed sample at ordinary temperature, is introduced either in the flow passage on the upstream side of the valve or in the flow passage in the valve to prevent the flow passage in the valve from clogging.

5 Claims, 1 Drawing Sheet

EXHAUST VALVE FOR SUPERCRITICAL FLUID CHROMATOGRAPH

FIELD OF THE INVENTION

The present invention relates to a supercritical fluid chromatograph; that is, an apparatus for carrying out supercritical fluid chromatography (SFC). More particularly, it relates to an SFC apparatus capable of preventing clogging of the flow passage of the constant-pressure release valve acting to maintain the pressure inside the system constant.

BACKGROUND OF THE INVENTION

In recent years, supercritical fluid chromatography (SFC), which is characterized by high resolution and short analysis time and capability of analyzing nonvolatile and thermally unstable chemical species, has attracted attention. One example of such SFC is disclosed in *Analytical Chemistry*, Vol. 54, No. 4, April 1982, pp. 736–740.

FIG. 1 is a schematic drawing showing the essential structure of an SFC apparatus. This apparatus comprises a pressure vessel 1 filled with gas, a liquid-delivering pump 2 equipped with a chiller, an injector 3, a microcolumn 4, an oven 5, an UV detector 6, and a constant-pressure release valve 7.

In the operation of this apparatus, the gas inside the pressure vessel 1 is pressurized to about or above its critical point by the pump 2 having the chiller. The pressurized gas, or mobile phase, is introduced into the column 4 at a constant flow rate. If the gas is $CO_2$, it is pressurized above the critical point of $CO_2$, i.e., above 73 atm., by the pump 2 and then forced into the column 4. The temperature of the inside of the column 4 is kept above the critical point of $CO_2$, or above 31° C., by the oven 5 and, therefore, a supercritical fluid of $CO_2$ is formed inside the column. Under this condition, a sample is injected from the injector 4. The sample is then dissolved in the supercritical fluid, developed, and separated in the column. The separated eluates are successively sent to the UV detector 6 and detected. Subsequently, they are discharged to the atmosphere via the constant-pressure release valve 7. Where the mobile phase is an organic solvent that is in liquid phase at ordinary temperature, such as hexane, it is not necessary to liquify the mobile phase and so the pump 2 is not required to have a chiller. Where a sample which is not readily dissolved in a supercritical fluid of $CO_2$ is analyzed, $CO_2$ gas to which a modifier such as alcohol has been added is used as the mobile phase. The constant-pressure release valve 7 is installed to maintain the inside of the flow passage system at a certain pressure exceeding the critical point.

Since the open end, or the discharge side, of the constant-pressure release valve is at the atmospheric pressure, while the mobile phase kept at a high pressure is passing into the valve, the pressure rapidly decreases, and the supercritical condition is no longer retained. Consequently, the sample which was dissolved in the supercritical fluid is separated out and deposited in the valve. The sample deposits in the discharge passage of the release valve and clogs it up. This varies the pressure inside the flow passage system of the apparatus, thus making the base line of the resulting chromatogram unstable. In the worst case, the discharge passage of the release valve is completely clogged up with the deposited sample, and the pressure inside the flow passage system increases. Then, the reproducibility and the separability deteriorate, whereby the sample cannot be analyzed.

SUMMARY OF THE INVENTION

It is an object of the present invention to provide a supercritical fluid chromatograph in which samples are prevented from depositing in and clogging up the discharge passage of the constant-pressure release valve.

The above object is achieved by an apparatus which discharges eluates via a constant-pressure release valve after the eluates are separated and analyzed by supercritical fluid chromatography. The apparatus is characterized in that a solvent is introduced either in the flow passage on the upstream side of the release valve or in the flow passage inside the valve. In one embodiment of a supercritical chromatography system, a separation column, an eluate detector at the outlet end thereof, and a constant-pressure release valve are positioned to allow flow of the supercritical fluid carrying the components of the sample being analyzed from the column and through the detector while maintaining pressure in the column and detector. The valve comprises a valve body with an inlet passage connected to the detector and an outlet passage. A bore in the valve body is in communication with the inlet passage and outlet passage. A bore defines a valve seat. A closure means is slidable in said bore for resting on the valve seat to block flow of eluates between the inlet and outlet passages. A diaphragm is positioned at an end of the bore opposite the valve seat. Means are provided to bias the diaphragm against the closure means to thereby bias the closure means against the valve seat. Means are further provided for introducing a solvent effective near atmospheric pressure to release valve such that components in the eluates will not deposit in the bore or the outlet passage of said release valve.

Other objects and features of the invention will appear in the course of the description thereof which follows.

DETAILED DESCRIPTION OF THE INVENTION

Figure 1:
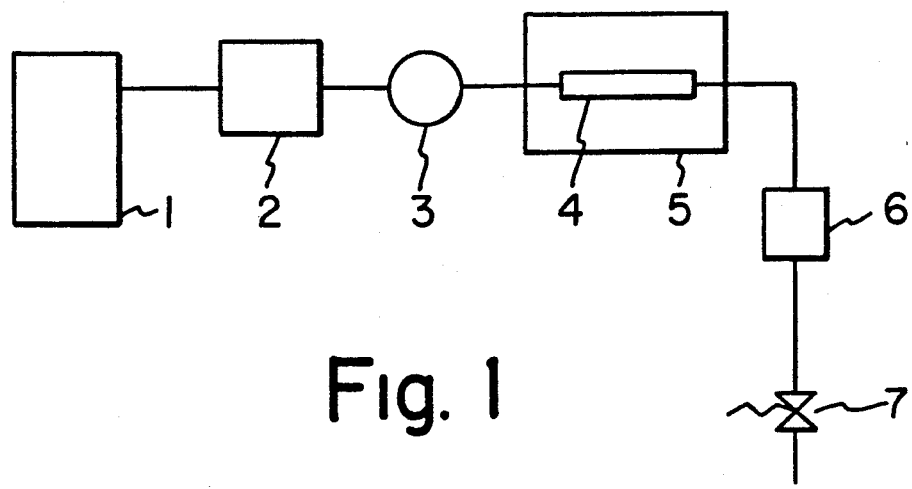
FIG. 1 is a block diagram of a supercritical fluid chromatograph.
Figure 2:
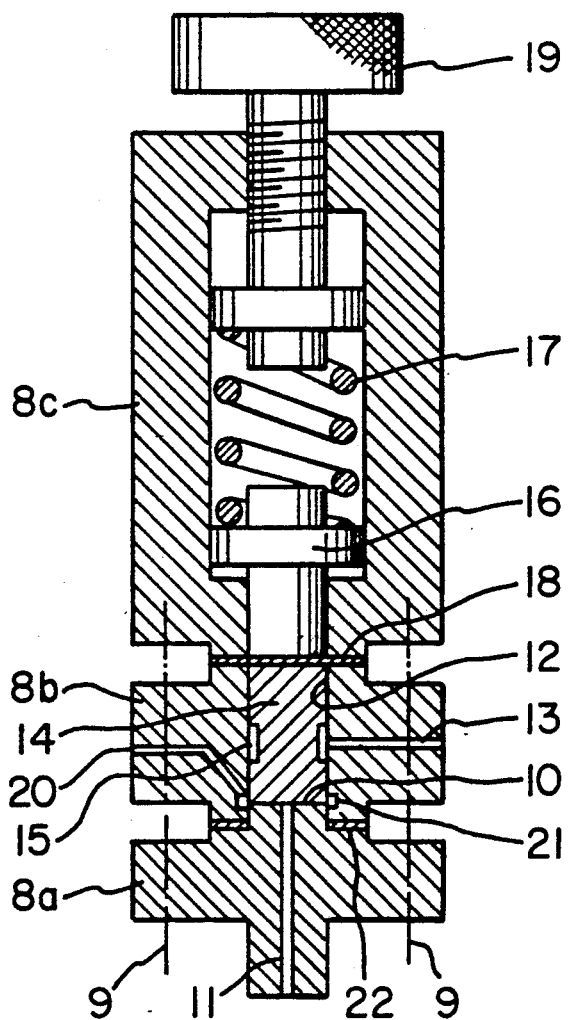
FIG. 2 is a cross-sectional view of a constant-pressure release valve delivering liquid at a very small flow rate for use in a supercritical fluid chromatograph according to the invention.

Referring to FIG. 2, there is shown a constant-pressure release valve for delivering liquid at a very small flow rate typical of SFC. This valve is used at the outlet of a supercritical fluid chromatograph. The release valve includes a valve body comprising first section 8a, second section 8b, and a third section 8c. These sections are stacked and coupled together by bolts 9 as indicated by the dot-and-dash lines. A specularly polished, planar valve seat 10 is formed in the center of an interior surface of the first section 8a. An inlet port 11 passes through the first section and is arranged to be connected to the UV detector 6 shown in FIG. 1. The port opens through the center of the valve seat 10.

The second section 8b is provided with a central bore 12. A discharge port 13 communicating with the inlet port 11 via the bore 12 is formed in the side wall of the second section 8b. A rodlike valve member 14 is inserted in the bore 12 so as to be slidable. In one position the valve member blocks passage of fluid from the inlet port 11 to the discharge port 13. The lower end surface of the valve member 14 that is opposite to the valve seat 10 is flat and specularly polished in the same way as the valve seat 10. This lower end surface can be brought into intimate contact with the valve seat 10. The length of the valve member 14 approximates the length of the bore 12 formed in the second section 8b. An annular groove 15 is formed in the outer portion of the valve member 14 which is opposed to the discharge port 13.

A piston 16 and a spring 17 are mounted inside the section 8c of the valve body to press the valve member 14 against the valve seat 10. A disk-like, flexible, thin film or diaphragm 18 is interposed between the piston 16 and the valve member 14. The fringe portion of the film 18 is held between the second section 8b and the third section 8c. The film 18 serves as a sealing member between the piston 16 and the atmosphere. The upper end of the spring 17 is in contact with a set screw 19 that is threaded into the third section 8c.

The second section 8b of the valve body is provided with a solvent inlet passage 20. One end of the passage 20 is connected with an annular recess 21 formed around the valve seat 10 with which the outer periphery of the valve member 14 is in contact. The other end of the passage 20 is connected via a pipe (not shown) and a liquid-delivering pump (not shown) with a vessel (not shown) filled with a solvent. This solvent may be an organic solvent which can readily dissolve the analyzed sample at ordinary temperatures and atmospheric pressure, such as toluene, dichloromethane, or benzene.

A sealing metallic gasket 22 is installed at the interface between the first section 8a and the second section 8b of the valve body. Where the first and the second sections are fabricated integrally, the gasket can be dispensed with. It is necessary that the materials of the thin film 18 and the gasket 22 be unreactive and insoluble in the presence of the supercritical fluid used, for example, stainless steel SUS316 defined by the Japanese Industrial Standard.

In this structure, the set screw 19 is rotated to apply a downward force $F_1$, to the spring 17. The force corresponds to a desired pressure of the mobile phase flowing through the flow passage system of the SFC apparatus. Thus, the valve member 14 is brought into intimate contact with the valve seat 10, and the inlet port 11 is blocked, from the discharge port 13. During the operation of the SFC apparatus, the force $F_2$ due to the pressure of the mobile phase becomes equal to the force $F_1$ of the spring 17. Under this condition, the valve member 14 moves upward against the depressing force of the spring 17 to form a desired gap between the valve seat 10 and the valve member 14. As a result, the mobile phase entering from the inlet port passes through the gap between the valve seat 10 and the valve member 14 and the gap between the second section 8b and the valve member 14. Finally, the mobile phase is discharged from the discharge port 13. Hence, the pressure of the mobile phase is kept at a preselected pressure.

A solvent which easily dissolves the sample is continuously introduced via the inlet port 20 into the recess 21 formed at the end of the gap between the valve seat 10 and the valve member 14. Therefore, if the pressure of the mobile phase drops and permits the sample to deposit while the mobile phase is passing through the gap between the valve seat and the valve member, the deposited sample is dissolved in the organic solvent and discharged from the discharge port 13 together with the solvent. Preferably, the solvent is an organic solvent that dissolves the components of the sample being analyzed at ordinary temperatures and pressures; that is, near room temperature and atmosphere pressure. Hence, it is unlikely that the sample will deposit and remain between the second section and the valve member to thereby clog up the flow passage.

In the present example, the SFC apparatus employs a microcolumn and a constant-pressure release valve having the planar valve member 14. This permits the thin film 18, or a sealing diaphragm, to be installed between the valve member 14 and the atmosphere, or the piston 16. Specifically, the microcolumn delivers a mobile phase at a quite small flow rate of 1 to 100 $\mu l$/min., for example. Therefore, if the pressure inside the flow passage system of the apparatus is set to hundreds of $Kg/cm^2$, for example, then the valve member moves a very slight distance on the order of microns or submicrons off the valve seat 10. Consequently, even though the valve seat moves up and down, the thin film is not destroyed. Since no external force such as a frictional force is applied to the valve member, because of the use of the seal in the form of a diaphragm, the pressure can be accurately controlled at very small flow rates.

It is to be noted that the foregoing description relates to only a preferred embodiment of the invention, and that various changes and modifications may be made therein. In the above example, the solvent dissolving the sample deposited by a decrease in the pressure of the mobile phase is supplied to the valve seat. The invention is not limited to this configuration. For instance, the solvent may be introduced close to the discharge port 13. Also, the solvent may be introduced in the inlet port 11 formed in the first section 8a of the valve body. In this case, it is necessary to introduce the solvent at substantially the same pressure as the liquid conveying the mobile phase.

In the above example, the mobile phase is introduced at a very small flow rate. The invention is not restricted to this scheme. The invention is applicable to an SFC apparatus in which a mobile phase is introduced at a large flow rate. In this case, the constant-pressure release valve is not limited in structure to the valve shown in FIG. 2. A commercially adaptable constant-pressure release valve configured according to the teachings of this invention could also be used.

As described in detail thus far, in accordance with the present invention, a solvent which readily dissolves a sample is introduced either in the flow passage in constant-pressure release valve or in the flow passage on the upstream side of the valve. Therefore, if the sample is deposited due to a pressure decrease produced when the mobile phase passes through the release valve, then the deposited sample is dissolved in the solvent and discharged to the atmosphere along with the solvent. For this reason, the deposited sample does not remain in the release valve. Hence, it does not clog up the valve, unlike in the prior art apparatus. Consequently, the pressure inside the flow passage system of the SFC apparatus is maintained at a desired predetermined pressure. Thus, the base line of the chromatogram is prevented from varying. Also, deterioration in reproducibility and resolution which would have been heretofore caused by pressure increases can be prevented.

Having thus described the invention in the detail and particularity required by the Patent Laws what is desired to be protected by Letters Patent is set forth in the following claims.

What is claimed is:

1. In a supercritical fluid chromatograph having a chromatographic column through which a mobile phase carrying eluates extracted from a sample is passed, means for introducing the mobile phase and sample to one end of the column at an elevated pressure, means at the other end for analyzing components present in eluates separated and detected by supercritical fluid chromatography, and a relief valve having a fluid passage therein positioned downstream of the means for analyzing, said mobile phase being maintained in the column and means for analyzing at supercritical conditions, said relief valve discharging the mobile phase and eluates while maintaining the pressure of the mobile phase in the column above a preselected pressure, the improvement comprising means for introducing a solvent effective near atmospheric pressure in the relieve valve fluid passage such that components in the eluates will not deposit in the relief valve fluid passage.

2. The supercritical fluid chromatograph of claim 1, wherein said solvent is an organic solvent which readily dissolves the sample being analyzed near room temperature.

3. In a supercritical chromatography system having a separation column with an outer end and an eluate detector in communication with the outlet end of the column, said eluate detector having an inlet and an outlet, means for introducing a mobile phase and sample to the column at an elevated pressure, a constant-pressure relief valve positioned at the outlet of the detector to allow flow of the supercritical fluid carrying the components of the sample being analyzed from the column and through the detector while maintaining pressure in the column and detector, said valve comprising a valve body with an inlet passage connected to the outlet of the detector and an outlet passage, a bore in said valve body in communication with the inlet passage and outlet passage, said bore defining a valve seat, a closure means slidable in said bore for resting on said valve seat to block flow of eluates between the inlet and outlet passages, a diaphragm at an end of said bore opposite the valve seat, means to bias the diaphragm against said closure means to thereby bias the closure means against the valve seat, means for introducing a solvent effective near atmospheric pressure to the release valve such that components in the eluates will not deposit in the bore or the outlet passage of said release valve.

4. The system according to claim 3, wherein the solvent is an organic solvent which readily dissolves the sample being analyzed near room temperatures.

5. The system according to claim 3, wherein the solvent is introduced to the relief valve around the outer periphery of the valve seat.

* * * * *

UNITED STATES PATENT AND TRADEMARK OFFICE
CERTIFICATE OF CORRECTION

PATENT NO.   :  5,031,448
DATED        :  July 16, 1991
INVENTOR(S)  :  Toshinori Saito It is certified that error appears in the above-identified patent and that said Letters Patent is hereby corrected as shown below:

Column 4 Line 48 "adaptable" should read --available--.

Signed and Sealed this

Seventeenth Day of November, 1992

Attest:

DOUGLAS B. COMER

*Attesting Officer*        Acting Commissioner of Patents and Trademarks